United States Patent
Salehi (10) Patent No.: US 10,456,155 B2
(45) Date of Patent: Oct. 29, 2019

(54) TISSUE SHAVER AND METHODS OF USE

(71) Applicant: NEUROENTERPRISES, LLC, Port Barrington, IL (US)

(72) Inventor: Sean A. Salehi, Chicago, IL (US)

(73) Assignee: NeuroEnterprises, LLC, Chicago, IL (US)

( * ) Notice: Subject to any disclaimer, the term of this patent is extended or adjusted under 35 U.S.C. 154(b) by 184 days.

(21) Appl. No.: 15/658,735

(22) Filed: Jul. 25, 2017

(65) Prior Publication Data
US 2017/0319225 A1 Nov. 9, 2017

Related U.S. Application Data (63) Continuation of application No. PCT/US2016/022375, filed on Mar. 14, 2016.

(60) Provisional application No. 62/177,554, filed on Mar. 19, 2015.

(51) Int. Cl.
| | | |
|---|---|---|
| A61B 17/32 | (2006.01) |
| A61B 17/16 | (2006.01) |
| A61B 17/00 | (2006.01) |
| A61B 90/00 | (2016.01) |
| F16H 37/16 | (2006.01) |

(52) U.S. Cl.
CPC .... *A61B 17/32002* (2013.01); *A61B 17/1671* (2013.01); *A61B 2017/00261* (2013.01); *A61B 2017/320004* (2013.01); *A61B 2090/08021* (2016.02); *F16H 37/16* (2013.01)

(58) Field of Classification Search
CPC .......... A61B 17/32002; A61B 17/1671; A61B 2017/00261; A61B 2017/320004; A61B 2090/08021; F16H 37/16
See application file for complete search history.

(56) References Cited

U.S. PATENT DOCUMENTS

| | | | |
|---|---|---|---|
| 2002/0058944 A1* | 5/2002 | Michelson | A61B 17/1671 606/79 |
| 2005/0159080 A1 | 7/2005 | Fong et al. | 451/5 |
| 2007/0060936 A1* | 3/2007 | Benavitz | A61B 17/1633 606/180 |
| 2009/0048485 A1* | 2/2009 | Heisler | A61B 17/32002 600/127 |
| 2011/0004215 A1* | 1/2011 | Bradley | A61B 17/1633 606/84 |
| 2011/0196404 A1 | 8/2011 | Dietz et al. | 606/169 |

FOREIGN PATENT DOCUMENTS

EP 1518492 3/2005

OTHER PUBLICATIONS

International Preliminary Report on Patentability, PCT Application No. PCT/US16/22375, pp. 1-8 (Sep. 28, 2017).

\* cited by examiner

*Primary Examiner* — George J Ulsh
(74) *Attorney, Agent, or Firm* — J. Peter Paredes; David G. Rosenbaum; Rosenbaum IP, P.C.

(57) ABSTRACT

A tissue shaver and methods of use is disclosed. The tissue shaver operates to remove tissue.

16 Claims, 4 Drawing Sheets

TISSUE SHAVER AND METHODS OF USE

CROSS REFERENCE TO RELATED APPLICATIONS

This application claims priority to and is a continuation from PCT Application Serial No. PCT/US2016/022375, filed Mar. 14, 2016, which claims priority from U.S. Provisional Application Ser. No. 62/177,554, filed Mar. 19, 2015, all of which are herein incorporated by reference in their entireties.

BACKGROUND

The invention generally relates to instruments for tissue removal and more specifically to instruments for removing tissue material.

A person may develop any one of a variety of debilitating spinal conditions and diseases. For example, when the outer wall of the disc (i.e., the annulus fibrosis) becomes weakened through age or injury, it may tear allowing the soft inner part of the disc (i.e., the nucleus pulposus) to bulge out, forming a herniation. The herniated disc often pinches or compresses the adjacent nerve root against a portion of the vertebra, resulting in weakness, tingling, numbness, or pain in the back, legs or other areas.

Often, inflammation of the nerve root from disc herniation can be treated successfully by nonsurgical means, such as bedrest, therapeutic exercise, oral anti-inflammatory medications or epidural injection of corticosterioids, and anesthetics. In some cases, however, the disc tissue is irreparably damaged, in which case, surgery is the best option.

Discectomy, which involves removing all, or a portion, of the affected disc, is the most common surgical treatment for ruptured or herniated discs of the lumbar spine. In most cases, a laminotomy or laminectomy is performed to visualize and access the affected disc. Once the vertebrae, disc, and other surrounding structures can be visualized, the surgeon will remove the section of the disc that is protruding from the disc wall and any other offending disc fragments that may have been expelled from the disc. In some cases, the entire disc may be removed, with or without a bony fusion or arthroplasty (disc nucleus replacement or total disc replacement).

Open discectomy is usually performed under general anesthesia and typically requires at least a one-day hospital stay. During this procedure, a one-to-two inch incision in the skin over the affected area of the spine is made. Muscle tissue may be separated from the bone above and below the affected disc, while retractors hold the wound open so that the surgeon has a clear view of the vertebrae and disc and related structures. The disc or a portion thereof can then be removed using standard medical equipment, such as rongeurs and curettes.

Because open discectomy requires larger incisions, muscle stripping or splitting, more anesthesia, and more operating, hospitalization, and a longer patient recovery time, the trend in spine surgery is moving towards minimally invasive surgical techniques, such as microdiscectomy and percutaneous discectomy.

Microdiscectomy uses a microscope or magnifying instrument to view the disc. The magnified view may make it possible for the surgeon to remove herniated disc material through a smaller incision (about twice as small as that required by open discectomy) with smaller instruments, potentially reducing damage to tissue that is intended to be preserved.

Percutaneous discectomy is often an outpatient procedure that may be carried out by utilizing hollow needles or cannulae through which special instruments can be deployed into the vertebra and disc in order to cut, remove, irrigate, and aspirate tissue. X-ray pictures and a video screen and computer-aided workstation may be used to guide by the surgeon into the treatment region. Improved imaging and video or computer guidance systems have the potential to reduce the amount of tissue removal required to access and treat the injured tissue or structures. Sometimes an endoscope is inserted to view the intradiscal and perivertebral area.

Besides disc herniations, other debilitating spinal conditions or diseases may occur. For example, spinal stenosis, which results from hypertrophic bone and soft tissue growth on a vertebra, reduces the space within the spinal canal. When the nerve roots are pinched, a painful, burning, tingling, and/or numbing sensation is felt down the lower back, down legs, and sometimes in the feet. The spinal canal has a rounded triangular shape that holds the spinal cord without pinching. The nerve roots leave the spinal canal through the nerve root canals, which should be free of obstruction. Hypertrophic bone growth (e.g., bone spurs, osteophytes, spondylophytes) within the spinal canal, and specifically from the diseased lamina and proximate facet joints may cause compression of the nerve roots, which may contribute or lead to the pain of spinal stenosis. Spinal stenosis may be treated by performing a laminectomy or laminectomy in order to decompress the nerve root 36 impinged by the bone growth 48. Along with the laminectomy, a foraminotomy, (i.e., enlarging of the channel from which the nerve roots 36 exit is performed). Depending on the extent of the bone growth, the entire lamina and spinal process may be removed.

Thus, it can be appreciated that in many spinal treatment procedures, bone and/or disc tissue must be removed in order to decompress neural tissue or rebuild the bony vertebra or intervertebral disc. In the case of target bone tissue that is adjacent spinal tissue, a physician is required to exercise extreme care when cutting away the target bone tissue (e.g., during a laminectomy and foraminotomy), such that injury to spinal tissue can be prevented. A physician may have difficulty controlling existing bone removal devices, however, and may unintentionally remove healthy bone tissue or injure spinal tissue during use. This problem is exacerbated with percutaneous treatments, which, although less invasive than other procedures, limit the range of motion of the cutting instrument, thereby further limiting the control that the physician may have during the bone cutting procedure. The present invention solves this problem and well as others.

SUMMARY OF THE INVENTION

Provided herein are systems, methods and apparatuses for a tissue shaver. A tissue shaver comprises an outer housing including a proximal end and a distal end and a longitudinal axis disposed there between; a cutting burr including a longitudinal shaft with a proximal end and a distal end, and a burr on the distal end of the longitudinal shaft, the longitudinal shaft operably coupled with a plunger including a distal end and a proximal end, and the longitudinal shaft and plunger coaxially disposed within the outer housing, and the cutting burr rotates relative to the cutting burr to provide a cutting action; a first geared wheel operably coupled with the proximal end of the longitudinal shaft; a second geared wheel rotatably coupled with the distal end of the plunger;

and the second geared wheel rotatably coupled with the first geared wheel; a spring fixedly coupled with the distal end of the plunger as to proximally bias the plunger when the plunger is translated distally; and a handle operably coupled with the proximal end of the plunger, wherein the plunger is translated distally to along the longitudinal axis of the outer housing as to rotate the second geared wheel and rotate the cutting burr about the longitudinal axis.

A method of shaving tissue using the tissue shaver is disclosed, comprising: introducing the outer housing a small incision in the back and into a herniated disc such that its distal end of the outer housing is placed adjacent the distal-most region of the target tissue; translating the plunger distally by a force from a user as to rotate the burr about a rotational axis; biasing the plunger proximally by the spring to cause further rotation of the burr, which causes the burr to rotate in the opposite direction and tissue is removed by the rotating burr by both the distal and proximal translation of the plunger; and suctioned the removed tissue from the herniated disc by way of the open mesh design of the burr and the suction or vacuum action created by the plunger.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

In one embodiment, the tissue shaver addresses the issue of recurrent herniation by shaving down the annular bulge without excising it causing further instability of the disc. The tissue shaver shaves (files down) the bulging portion of the disc without excising it. The tissue shaver may be used in arthroscopic, orthopedic, or endoscopic surgery to remove or treat human tissue. In one embodiment, the tissue shaver operates to remove tissue. In other embodiments, other tissue, bone, ligaments, skin, connective, muscle, nervous, or epithelial tissue may be removed and shaved down by the tissue shaver.

Figure 1A:
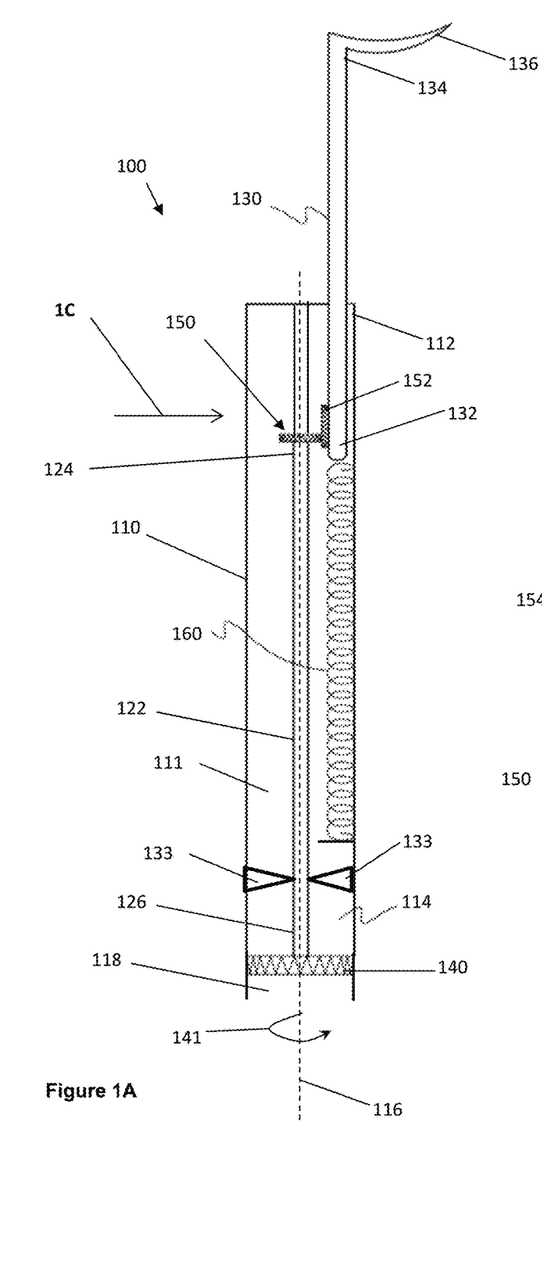
FIG. 1A is a side view of the tissue shaver, according one embodiment.
Figure 1B:
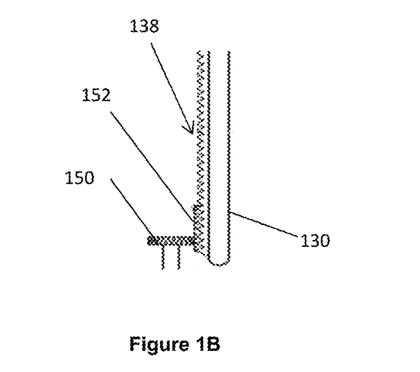
FIG. 1B is an enlarged side view of the plunger engaged with the second geared wheel and the first geared wheel.
Figure 1C:
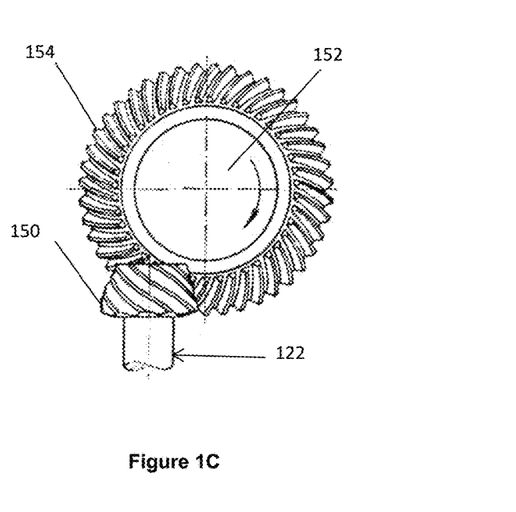
FIG. 1C is a view from 1C in FIG. 1A showing the first geared wheel coupled with the second geared wheel.
Figure 2A:
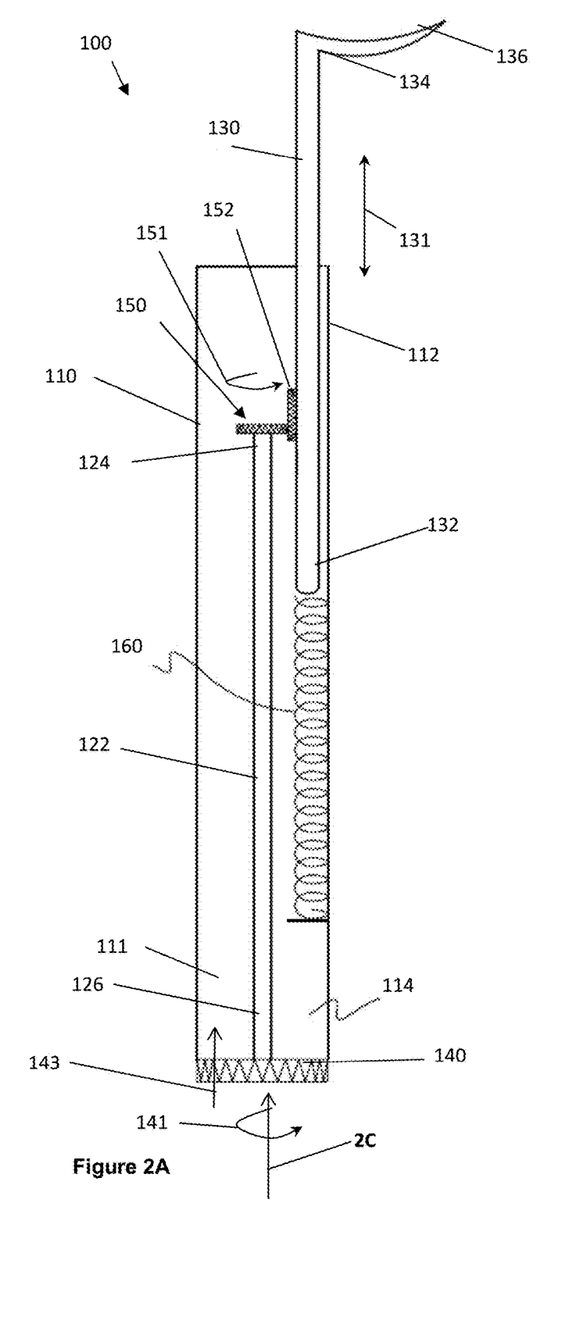
FIG. 2A is a side view of the tissue shaver, according one embodiment.
Figure 2B:
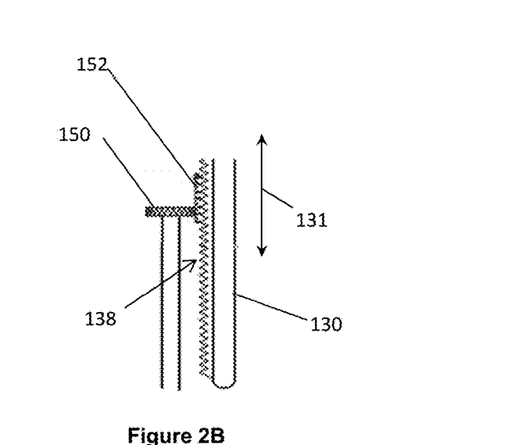
FIG. 2B is an enlarged side view of the plunger engaged with the second geared wheel and the first geared wheel when the plunger longitudinally translates toward the distal end of the housing.
Figure 2C:
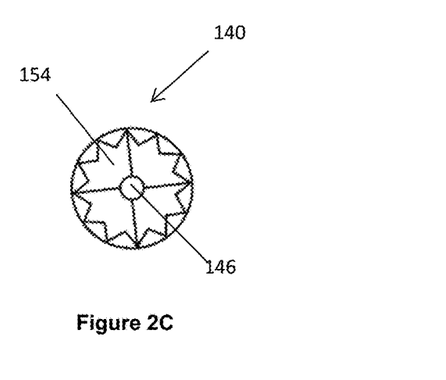
FIG. 2C is a view from 2C in FIG. 2A showing the face of the cutting burr in an open mesh design.
Figure 3A:
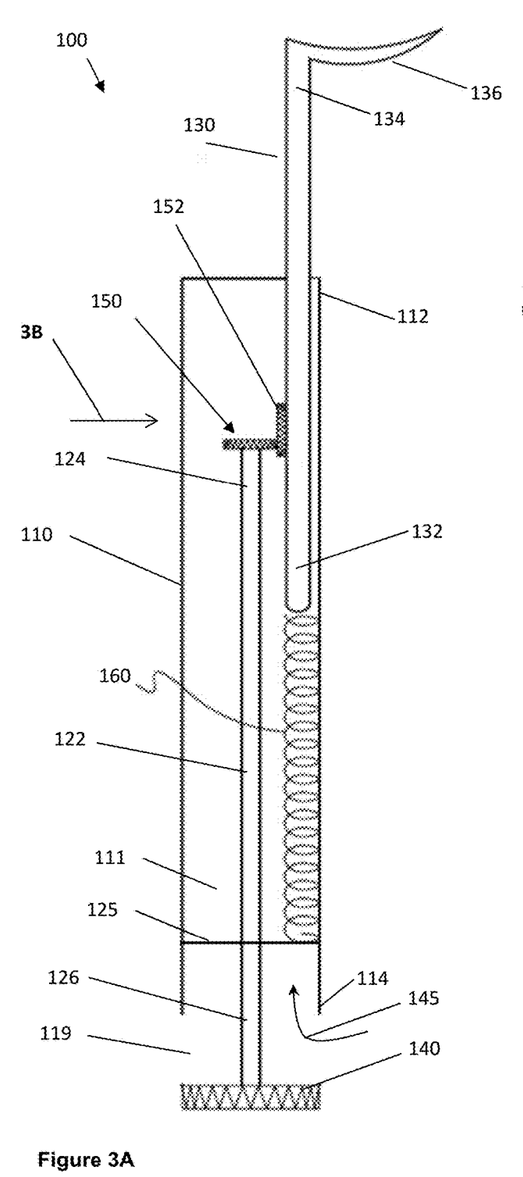
FIG. 3A is a side view of the tissue shaver, according one embodiment.
Figure 3B:
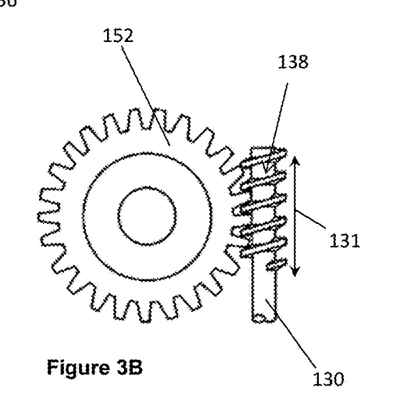
FIG. 3B is a view from 3B in FIG. 3A showing the second geared wheel coupled with the plunger.
Figure 3C:
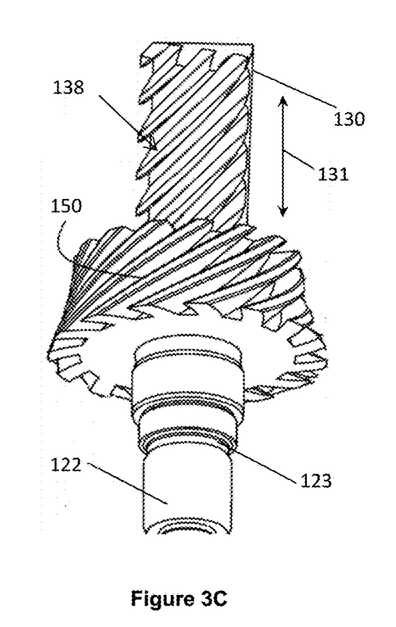
FIG. 3C is a perspective view showing the first geared wheel coupled plunger.

Generally speaking, the tissue shaver 100 comprises an outer housing 110 and a cutting burr 120 coaxially disposed within the outer housing 110, as shown in FIGS. 1-3. The outer housing 110 includes a proximal end 112 and a distal end 114 and a longitudinal axis 116 disposed therebetween. The cutting burr 120 is operably coupled with a plunger 130 as to rotatably move the cutting burr to provide a cutting action. The cutting burr 120 includes a longitudinal shaft 122 with a proximal end 124 and a distal end 126. The cutting burr 120 includes a burr 140 on the distal end 126 of the longitudinal shaft 122. There is a gap or space 118 between the distal end of the burr 140 and the distal end of the outer housing 114. The burr 140 includes a plurality of cutting teeth 142 that cuts and shaves tissue material by rotation of the burr 140 about the longitudinal axis shown by arrow 141. In one embodiment, the outer housing 110 includes a lumen 111 and a plurality of bearings 133 disposed within the lumen 111 as to allow the rotation of the burr 140 and the shaft 120 to occur without wobbling. The proximal end 124 of the longitudinal shaft 122 includes a first geared wheel 150. The plunger 130 includes a distal end 132 and a proximal end 134 and a second geared wheel 152 rotatably coupled to the distal end 132. The second geared wheel 152 is operably coupled with the first geared wheel 150. The distal end 132 of the plunger 130 is fixedly coupled with a spring 160 as to proximally bias the plunger 130 when the plunger 130 is translated distally. The proximal end of the 134 includes a handle 136 for a user to grasp or push the plunger along the longitudinal axis 116 of the outer housing 110.

In operation, the plunger 130 is translated distally towards the distal end 114 of the outer housing by operation of the user via the handle 136 and a force. The plunger 130 rotates the second geared wheel 152 by operation of geared teeth 138 located on a surface of the plunger 130. The second geared wheel includes a plurality of gears located around the circumference of the second geared wheel 152. The second geared wheel 152 includes a crown gear 154 on the top surface of the second geared wheel 152. The teeth of the crown gear project at right angles to the plane of the second geared wheel 152; in their orientation the teeth resemble the points on a crown. The crown gear 154 meshes accurately with the teeth of the first geared wheel 150, as shown in FIG. 1C. Rotation of the first geared wheel 150 in the direction of arrow 151 rotates the shaft 122 and rotates the burr 140 in the direction of arrow 141, as shown in FIGS. 2A-2B. The distal translation of the plunger 130 also distally translates the longitudinal shaft 122 and the burr 140 to close the gap 118 such that the burr 140 is flush with the distal end 114 of the outer housing 110, as shown in FIG. 2A. The longitudinal translation of the plunger 130 in the direction of arrow 131 thus rotates the burr 140 in the direction of arrow 141 to sufficiently cut tissue. The spring 160 proximally bias the plunger 130 when the plunger 130 is translated distally and causes further rotation of the shaft 122 and the burr 140 in the opposite direction. A user then pushes the handle 136 and distally translates the plunger 130 towards the distal end 114 of the outer housing to cause the burr 140 to rotate again and provide a cutting or shaving action.

In one embodiment, the bearing 133 may be selected from different types of bearings depending on the operating principle and selected from a plain bearing, a rolling element bearing, a jewel bearing, a fluid bearing, a magnetic bearing, and a flexure bearing. A plain bearing is also known by the specific styles: bushing, journal bearing, sleeve bearing, and rifle bearing. A rolling-element bearing is a ball bearings and roller bearings. A jewel bearing, in which the load is carried by rolling the axle slightly off-center. A fluid bearing, in which the load is carried by a gas or liquid. A magnetic bearing, in which the load is carried by a magnetic field. And flexure bearing, in which the motion is supported by a load element which bends. The shaft 122 may include a circular indent 123, as shown in FIG. 3C, as to receive the bearings 133 and to allow for near frictionless rotation of the shaft 122.

In one embodiment, as shown in FIG. 2C, the cutting burr 140 has an open mesh design, whereby the cutting burr includes a central opening 144 allowing the accumulation of the cut tissue or disc material to pass into a shaft opening 146. With the cutting burr 140 flush with the distal end 114 of the outer housing 110, the longitudinal translation of the plunger 130 may create a vacuum or suction action through the shaft opening 146 or the central opening 144. The proximal translation of the plunger 130 may be longitudinally moved by the user to create a force in the direction of arrow 143 as shown in FIG. 2A, as to suck up cut tissue or disc material into a lumen 111 of the outer housing 110. The force may be between 1N and 5N.

As shown in FIG. 3A, an alternative embodiment, the burr 140 and the longitudinal shaft 122 may translate beyond the distal end 114 of the housing 110 such as to leave a gap or space 119 between the burr 140 and the distal end 114 of the housing 110. The gap or space 119 may collect cut tissue or disc material into the lumen 111 of the housing. The longitudinal translation of the plunger 130 may create a vacuum or suction action through the space 119 in the direction of arrow 145 as to collect cut tissue or disc material. A one way valve 125 located on the distal end of the outer housing within the lumen 111 may only allow the suction action to be in the direction of arrow 145 by not allowing air to be pushed distally from the one way valve 125. In another embodiment, a second one way valve may be located on the proximal end of the outer housing within the lumen 111, which may allow the suction action be in the direction of arrow 145 by not allowing air to be pushed distally away from the second one way valve.

In one embodiment, the outer housing 110 is made of plastic polymers, such as Acrylonitrile butadiene styrene (ABS). Other thermoplastics may be used such as Acrylic, Nylon, Polylactic acid (PLA), Polybenzimidazole, Polycarbonate, Polyether sulfone, Polyetherether ketone, Polyetherimide, Polyethylene, Polyphenylene oxide, Polyphenylene sulfide, Polypropylene, Polystyrene, Polyvinyl chloride, Teflon, and the like. To facilitate introduction through tissue, the housing 110 is preferably stiff (e.g., it can be composed of a stiff material, or reinforced with a coating or a coil to control the amount of flexing), so that the housing 110 can penetrate the tissue without being damaged. In one embodiment, the shaft, geared wheels, and plunger may be made of metal such as stainless steel, titanium alloys, shape memory metals, or cobalt alloys. In one embodiment, the handle is composed of a durable and rigid material that is ergonomically molded to allow a user to easily manipulate, push, and pull the plunger.

To maintain the correct surface speed and cutting conditions, the burr 140 may rotate at high speed, which may be thousands or tens of thousands of Rotations Per Minute (RPM). In one embodiment, different angles of the burr's cutting face with respect to the tissue or disc being cut may be made, such as between about 20°, 40°, 60° and 90°. The RPM may be adjusted by the force at which the plunger is pushed and thus causing rotation of the first geared wheel and the cutting burr. The RPM may be between about 100 and 10,000 RPM.

In one embodiment, the distal end 114 includes a diameter of 3 mm but the proximal end 112 is wider. The diameter of the cutting burr 140 may match the diameter of the distal end 114 such that the cutting burr 140 is flush with the distal end 114. As such, the diameter of the cutting burr 140 may be about 3 mm.

In one embodiment, the plunger and the second geared wheel act as a rack and pinion geared system, whereby the linear motion of the plunger converts linear motion into rotational motion. The second geared wheel acts as the "the pinion" and engages teeth on the plunger called "the rack"; linear motion applied to the rack causes the pinion to rotate relative to the rack, thereby translating the linear motion of the rack into rotational motion.

In another embodiment, the second geared wheel and the first geared wheel act as a hypoid gears, as shown in FIG. 1C, which resemble spiral bevel gears except the shaft axes do not intersect. The pitch surfaces appear conical but, to compensate for the offset shaft, are in fact hyperboloids of revolution. Hypoid gears are almost always designed to operate with shafts at 90 degrees. Depending on which side the shaft is offset to, relative to the angling of the teeth, contact between hypoid gear teeth may be even smoother and more gradual than with spiral bevel gear teeth, but also have a sliding action along the meshing teeth as it rotates and therefore usually require some of the most viscous types of gear oil to avoid it being extruded from the mating tooth faces, the oil is normally designated HP (for hypoid) followed by a number denoting the viscosity. Also, the pinion can be designed with fewer teeth than a spiral bevel pinion, with the result that gear ratios of 60:1 and higher are feasible using a single set of hypoid gears. In one embodiment, the gear ratio is between 60:1 and 200:1 as to create high rotation motion of the first geared wheel relative to the second geared wheel.

In another embodiment, the plunger 130 and the second geared wheel 152 operate as a worm drive, as shown in FIG. 3B, where the plunger 130 acts as the worm and the second geared wheel 152 acts as the worm gear. The worm drive is a gear arrangement in which a worm (which is a gear in the form of a screw) meshes with a worm gear (which is similar in appearance to a spur gear). The two elements are also called the worm screw and worm wheel. A worm gear is a species of helical gear, but its helix angle is usually somewhat large (close to 90 degrees) and its body is usually fairly long in the axial direction. These attributes give it screw like qualities. The worm gear includes at least one tooth persisting for a full rotation around the helix. A worm may have as few as one tooth. If that tooth persists for several turns around the helix, the worm appears, superficially, to have more than one tooth, but what one in fact sees is the same tooth reappearing at intervals along the length of the worm. The usual screw nomenclature applies: a one-toothed worm is called single thread or single start; a worm with more than one tooth is called multiple thread or multiple start. The helix angle of a worm is not usually specified. Instead, the lead angle, which is equal to 90 degrees minus the helix angle, is given.

In a worm-and-gear set, the worm can always drive the gear. Worm-and-gear sets that do lock are called self-locking, which can be used to advantage, as for instance when it is desired to set the position of a mechanism by turning the worm and then have the mechanism hold that position. If the gear in a worm-and-gear set is an ordinary helical gear only a single point of contact is achieved. If medium to high power transmission is desired, the tooth shape of the gear is modified to achieve more intimate contact by making both gears partially envelop each other. This is done by making both concave and joining them at a saddle point; this is called a cone-drive or "Double enveloping".

In an alternative embodiment, the plunger 130 is directly coupled with the first geared wheel 150, as shown in FIG. 3C. The plunger 130 includes geared teeth 138 and acts as a helical angle gear rack, while the first geared wheel 150 acts a helical pinion. Longitudinal translation in the direction of arrow 131 of the plunger 130 rotates the first geared wheel 150.

In an alternative embodiment, the plunger may operate as a roller screw, also known as a planetary roller screw or satellite roller screw, is a low-friction precision screw-type actuator, a mechanical device for converting rotational motion to linear motion, or vice versa. A roller screw is a mechanical actuator similar to a ball screw that uses rollers as the load transfer elements between nut and screw instead of balls. The rollers are typically threaded but may also be grooved depending on roller screw type. Providing more bearing points than ball screws within a given volume, roller screws can be more compact for a given load capacity while providing similar efficiency (75%-90%) at low to moderate speeds, and maintain relatively high efficiency at high speeds. Roller screws can surpass ball screws in regard to positioning precision, load rating, rigidity, speed, acceleration, and lifetime. Standard roller screw actuators can achieve dynamic load ratings above 130 tons of force (exceeded in single-unit actuator capacity only by hydraulic cylinders).

Figure 4A:
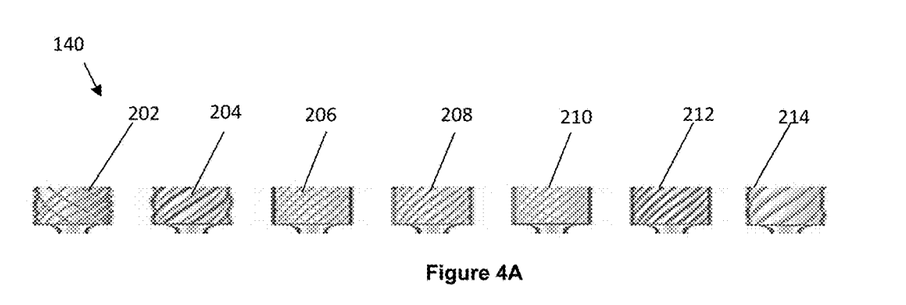
FIG. 4A are side views of alternative surfaces of the cutting burr.
Figure 4B:
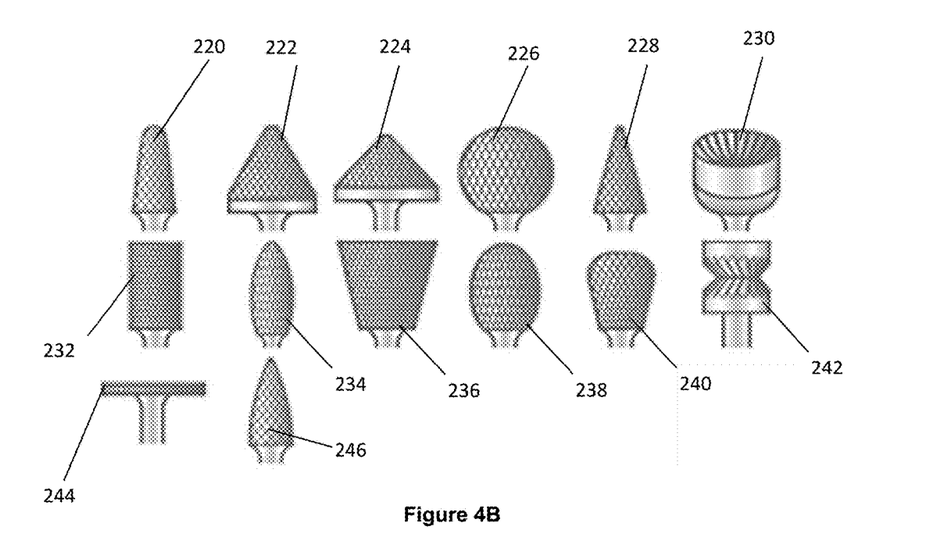
FIG. 4B are side views of alternative shapes of the cutting burr.

As shown in FIG. 4A, the burr 140 may include alternative cutting surfaces 200 may include: Clog-Resistant Double Cut 202, Clog-Resistant Single Cut 204, Diamond Cut 206, Double Cut 208, Fine Single Cut 210, Single Cut 212. The burr 140 may also assume alternative shapes, as shown in FIG. 4B, such as a 14 Degree Taper shape 220, a 60 Degree Cone 222, a 90 Degree Cone shape 224, a Ball-shape 226, a Cone-shape 228, a Cup-shape 230, a Cylindrical-shape 232, Flame-shape 234, Inverted Cone-shape 236, Oval-shape 238, Pear-shape 240, a W-shape 242, a Thin Disc-shape 244, or a tree-shape 246.

In performing a discectomy on a herniated disc and shaving down the bulging disc, the outer housing is introduced through a small incision in the back and into the herniated disc. In some cases, a laminectomy may have to be performed to access the disc and the outer housing may be used to bore through the lamina. Torsional and/or axial motion may be applied to the outer housing to facilitate boring of the lamina. An object may be used to tap again the handle to facilitate boring through the lamina. Alternatively, a stilette can be introduced through the outer housing lumen to create a passage through the lamina. Or, a separate drill or bone cutting device can be used to bore or cut a passage through the lamina prior to placement of the outer housing.

The outer housing of the tissue shaver is introduced into the disc, such that its distal tip is placed adjacent the distal-most region of the target tissue. In one case, it is distal to the herniation of the disc. Next, the plunger is translated distally by the user by a force as to rotate the burr about a rotational axis. At the same time, the plunger is biased proximally by the spring to cause further rotation of the burr, which causes the burr to rotate in the opposite direction. As a result, tissue is removed by the rotating burr by both the distal and proximal translation of the plunger. In effect, the burr removes a small disc of tissue at this point. It should be noted that, during the tissue removal procedure, the removed tissue is suctioned aspirated from the herniated disc by way of the open mesh design of the burr and the suction or vacuum action created by the plunger. Suction of the tissue is stored in the lumen of the housing.

Next, the outer housing is displaced in the proximal direction, and the tissue shaver is retracted. The steps may be repeated to remove another disc of tissue. After the discectomy has been completed (i.e., the herniated disc material has been removed, or in some cases, the entire herniated disc has been removed), the tissue shaver is removed from the patient's body. Alternatively, prior to total removal of the tissue shaver, and a therapeutic media, such as a drug or disc replacement material can be delivered through the lumen of the outer housing into the disc.

As can be understood by one skilled in the art, the tissue shaver 100 and/or any of its components may have any size, shape, length, thickness, height, weight, or any other parameters. Such parameters may be selected by the surgeon (or other qualified professional) for performance of specific procedures. Further, the tissue shaver 100 and/or any of its components may be manufactured from metal, plastic, synthetic material, or other suitable materials, or any combination thereof. In one embodiment, the tissue shaver 100 is composed of a metal alloy, titanium, nitinol, or stainless steel, or alternatively, any medical grade composite or ceramic.

In some embodiments, various lengths and configurations may also include various features to accommodate different applications for the tissue shaver 100. The tissue shaver 100 can be constructed of various materials to aid in radio translucency, strength, flexibility, and integration with anatomy, etc.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A tissue shaver comprising:
   an outer housing including a proximal end and a distal end and a longitudinal axis disposed therebetween;
   a cutting burr including a longitudinal shaft with a proximal end and a distal end, and the cutting burr on the distal end of the longitudinal shaft, the longitudinal shaft operably coupled with a plunger including a distal end and a proximal end, and the longitudinal shaft and plunger coaxially disposed within the outer housing, and the cutting burr rotates relative to the outer housing to provide a cutting action;
   a first geared wheel operably coupled with the proximal end of the longitudinal shaft;
   a second geared wheel rotatably coupled with the distal end of the plunger; and the second geared wheel rotatably coupled with the first geared wheel;
   a spring fixedly coupled with the distal end of the plunger as to proximally bias the plunger when the plunger is translated distally; and
   a handle operably coupled with the proximal end of the plunger, wherein the plunger is translated distally to along the longitudinal axis of the outer housing as to rotate the second geared wheel and rotate the cutting burr about the longitudinal axis.

2. The tissue shaver of claim 1, further comprising a gap between a distal end of the cutting burr and the distal end of the outer housing; and the distal translation of the plunger also distally translates the longitudinal shaft and the cutting burr to close the gap between a distal end of the cutting burr and the distal end of the outer housing such that the cutting burr is flush with the distal end of the outer housing.

3. The tissue shaver of claim 2 wherein the outer housing includes a lumen and a plurality of bearings disposed within the lumen and operably coupled with the longitudinal shaft as to allow the rotation of the cutting burr and the shaft to occur without wobbling.

4. The tissue shaver of claim 3, wherein the second geared wheel includes a plurality of geared teeth around the circumference of the second geared wheel and the second geared wheel includes a crown gear on the top surface of the second geared wheel; the plunger includes a plurality of geared teeth located on a surface of the plunger that mesh with the plurality of geared teeth around the circumference of the second geared wheel; and the first geared wheel includes a plurality of geared teeth that accurately meshes with the crown gear on the top surface of the second geared wheel; wherein longitudinal translation of the plunger rotates the second geared wheel, and rotation of the second geared wheel rotates the first geared wheel, and the rotation of the first geared wheel rotates the longitudinal shaft and the cutting burr; and the proximal translation of the plunger causes further rotation of the second geared wheel, first geared wheel, shaft, and the cutting burr.

5. The tissue shaver of claim 4, wherein the plurality of bearings are selected from the group consisting of a plain bearing, a rolling element bearing, a jewel bearing, a fluid bearing, a magnetic bearing, and a flexure bearing.

6. The tissue shaver of claim 5, wherein the cutting burr includes an open mesh design, a shaft opening, and a central opening allowing the accumulation of the cut tissue or disc material to pass into the shaft opening.

7. The tissue shaver of claim 6, wherein the cutting burr and the longitudinal shaft translate beyond the distal end of the housing such as to leave a gap between the cutting burr and the distal end of the housing, wherein the gap collects cut tissue material into the lumen of the housing by the longitudinal translation of the plunger creating a suction force through the gap; and a one way valve located within the lumen to not allow air to be pushed distally from the one way valve.

8. The tissue shaver of claim 6, wherein the longitudinal translation of the plunger creates a suction force through the shaft opening when the cutting burr is flush with the distal end of the outer housing and when the longitudinal translation of the plunger create the suction force through the shaft opening by the proximal translation of the plunger, as to suck up cut tissue material into the lumen of the outer housing; and a one way valve located within the lumen to not allow air to be pushed distally from the one way valve.

9. The tissue shaver of claim 8, wherein the cutting burr rotate at thousands or tens of thousands of Rotations Per Minute (RPM).

10. The tissue shaver of claim 9, wherein the second geared wheel is a pinion and the geared teeth of the plunger are a rack as to act as a rack and pinion geared system, whereby the linear motion of the plunger converts linear motion into rotational motion.

11. The tissue shaver of claim 9, wherein the second geared wheel is a spiral bevel gear and the first geared wheel is a spiral bevel gear as to act as a hypoid gear.

12. The tissue shaver of claim 9, wherein the plunger is a worm and the second geared wheel is a worm gear to act as a worm drive.

13. The tissue shaver of claim 9, wherein the cutting burr includes a cutting surfaces selected from the group consisting of may include: Clog-Resistant Double Cut, Clog-Resistant Single Cut, Diamond Cut, Double Cut, Fine Single Cut, and Single Cut.

14. The tissue shaver of claim 9, wherein the cutting burr includes a shape selected from the group consisting of the following shapes: a 14 Degree Taper shape, a 60 Degree Cone, a 90 Degree Cone shape, a Ball-shape, a Cone-shape, a Cup-shape, a Cylindrical-shape, Flame-shape, Inverted Cone-shape, Oval-shape, Pear-shape, a W-shape, a Thin Disc-shape, and a tree-shape.

15. A method of shaving tissue using the tissue shaver of claim 1, comprising:
   introducing the outer housing a small incision in the back and into a herniated disc such that its distal end of the outer housing is placed adjacent the distal-most region of the target tissue;
   translating the plunger distally by a force from a user as to rotate the cutting burr about a rotational axis;
   biasing the plunger proximally by the spring to cause further rotation of the cutting burr, which causes the cutting burr to rotate in the opposite direction and tissue is removed by the rotating cutting burr by both the distal and proximal translation of the plunger; and
   suctioned the removed tissue from the herniated disc by way of the open mesh design of the cutting burr and the suction or vacuum action created by the plunger.

16. A tissue shaver comprising:
   an outer housing including a proximal end and a distal end and a longitudinal axis disposed therebetween;
   a cutting burr including a longitudinal shaft with a proximal end and a distal end, and the cutting burr on the distal end of the longitudinal shaft, the longitudinal shaft operably coupled with a plunger including a distal end and a proximal end, and the longitudinal shaft and plunger coaxially disposed within the outer housing, and the cutting burr rotates relative to the outer housing to provide a cutting action;
   a first geared wheel rotatably coupled with the proximal end of the longitudinal shaft;
   a spring fixedly coupled with the distal end of the plunger as to proximally bias the plunger when the plunger is translated distally; and
   a handle operably coupled with the proximal end of the plunger, wherein the plunger is translated distally to along the longitudinal axis of the outer housing as to rotate the first geared wheel and rotate the cutting burr about the longitudinal axis.

* * * * *